(12) United States Patent
Iwakiri et al.

(10) Patent No.: US 8,406,377 B2
(45) Date of Patent: Mar. 26, 2013

(54) RADIOGRAPHIC APPARATUS AND METHOD

(75) Inventors: Naoto Iwakiri, Kanagawa-ken (JP);
Haruyasu Nakatsugawa,
Kanagawa-ken (JP); Naoyuki Nishino,
Kanagawa-ken (JP); Yasunori Ohta,
Kanagawa-ken (JP); Yutaka Yoshida,
Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 180 days.

(21) Appl. No.: 13/067,558

(22) Filed: Jun. 9, 2011

(65) Prior Publication Data

US 2011/0305321 A1 Dec. 15, 2011

(30) Foreign Application Priority Data

Jun. 10, 2010 (JP) ................................ 2010-132782

(51) Int. Cl.
*H05G 1/64* (2006.01)

(52) U.S. Cl. .................................................... 378/98.8

(58) Field of Classification Search .................... 378/19, 378/98.8, 98.5, 98.11
See application file for complete search history.

(56) References Cited

U.S. PATENT DOCUMENTS

| | | | |
|---|---|---|---|
| 2007/0034806 A1* | 2/2007 | Hornig | 250/370.08 |
| 2007/0069143 A1* | 3/2007 | Spahn | 250/370.09 |
| 2009/0272909 A1* | 11/2009 | Takenaka et al. | 250/370.09 |
| 2009/0304144 A1* | 12/2009 | Beyerlein et al. | 378/19 |
| 2009/0304145 A1* | 12/2009 | Schlomka | 378/19 |

FOREIGN PATENT DOCUMENTS

JP 2000-292598 10/2000

\* cited by examiner

*Primary Examiner* — Irakli Kiknadze
(74) *Attorney, Agent, or Firm* — Jean C. Edwards, Esq.; Edwards Neils PLLC (57) ABSTRACT

A timing to acquire a still image signal is controlled such that a sum (Tst+Trd) of a storage period Tst and a readout period Trd for the still image signal is an integral multiple (Ts+Tr=Tck×n, where n is an integer of 2 or greater) of a cycle Tck of a moving image capturing mode, when a detector controller acquires the still image signal while acquiring a moving image signal from a radiation detector during the cycle Tck (Ts+Tr) of the moving image capturing mode.

4 Claims, 8 Drawing Sheets

RADIOGRAPHIC APPARATUS AND METHOD

CROSS-REFERENCE TO RELATED APPLICATION

This application is based upon and claims the benefit of priority from Japanese Patent Application No. 2010-132782 filed on Jun. 10, 2010, of which the contents are incorporated herein by reference.

BACKGROUND OF THE INVENTION

1. Field of the Invention

The present invention relates to a radiographic apparatus and method for acquiring moving and still images with a radiation detector, which detects radiation that has passed through a subject and converts the detected radiation into a signal charge carrying image information.

2. Description of the Related Art

In the medical field, there have widely been used radiographic image capturing systems that apply radiation to a subject and guide the radiation that has passed through the subject to a radiation detector, which captures radiographic image information of the subject from the radiation. Known forms of radiation detector panels include a conventional radiation film for recording a radiographic image by way of exposure, and a stimulable phosphor panel for storing radiation energy representing radiographic image information in a phosphor, and reproducing the radiographic image information as stimulated light by applying stimulating light to the phosphor. The radiation film with radiographic image information recorded therein is supplied to a developing device to develop the radiographic image information. Alternatively, the stimulable phosphor panel is supplied to a reading device, which reads the radiographic image as a visible image.

During surgeries, contrast-enhanced imaging procedures, or bone fracture treatments, it is necessary to read radiographic image information from a radiation detector immediately after the radiographic image information has been captured for the purpose of quickly and appropriately treating the patient. As a radiation detector which meets such a requirement, there has been developed a radiation detector referred to as a flat panel detector (FPD) having a solid-state detector (also referred to as pixels) for converting radiation directly into an electric signals or converting visible light, which has been converted from radiation by a scintillator, into electric signals.

As disclosed in Japanese Laid-Open Patent Publication No. 2000-292598, a developed radiation detector is used to capture moving images (radioscopic images) and still images (general images) in the medical field. Moving images are used for observation in angiographic apparatus and bone fracture treatments, and still images are used to carry out accurate image diagnosis of body regions in question. There are certain instances in which the need arises to capture still images of a body region in order to carry out accurate observation and diagnosis while moving images are being captured of the body region.

Japanese Laid-Open Patent Publication No. 2000-292598 discloses a radiographic apparatus, which captures a moving image of a subject at successive frame intervals of t1 (t1=1/30 [sec], for example) while continuously applying X-rays at a low intensity level to the subject. The radiographic apparatus then stops applying X-rays for a given time of t2 (t2=2×t1), and thereafter captures a still image while applying X-rays at an intensity level which is roughly ten times higher than the low intensity level for an extremely short time tshort (tshort<<t1). Then, the radiographic apparatus stops applying X-rays for a given time of t3 (t3=3×t1−tshort), and thereafter captures a moving image at successive frame intervals of t1 while continuously applying X-rays at the low intensity level to the subject.

Japanese Laid-Open Patent Publication No. 2000-292598 states that when the radiographic apparatus is controlled to operate as described above, still images captured after the moving image has been captured do not contain a ghost of the moving image, and the moving image, which is captured after the still image has been captured, does not contain a ghost of the still image.

When a still image is captured between moving images, it is necessary to define a storage time during which X-rays are stored in pixels of a radiation detector, and a readout time during which the stored X-rays are read from the pixels while the moving images are captured. It also is necessary to define a storage time during which X-rays are stored in the pixels, and a readout time during which the stored X-rays are read from the pixels while the still image is captured. However, such storage and readout times are not defined in Japanese Laid-Open Patent Publication No. 2000-292598.

SUMMARY OF THE INVENTION

It is an object of the present invention to provide a radiographic apparatus and method for successively acquiring moving images, and also for acquiring still images of high quality between the moving images in synchronism with capturing of the radiographic images, by repeatedly capturing a moving image, a still image, and a moving image.

According to the present invention, there is provided a radiographic apparatus comprising a radiation detector having a matrix of pixels arranged in rows and columns for converting radiation into signal charges, storing the signal charges, and outputting the stored signal charges as a moving image signal or a still image signal, and a detector controller for switching the radiation detector into a moving image capturing mode or a still image capturing mode by controlling storage periods during which the radiation is converted into signal charges and the signal charges are stored, and readout periods during which the stored signal charges are read, wherein the detector controller controls a timing to acquire the still image signal, such that a sum of the storage period and the readout period for the still image signal is an integral multiple of a cycle of the moving image capturing mode, in a case where the detector controller acquires the still image signal while acquiring the moving image signal from the radiation detector during the cycle of the moving image capturing mode.

The timing to acquire the still image signal is controlled such that the sum of the storage period and the readout period for the still image signal is an integral multiple of the cycle of the moving image capturing mode, in a case where the detector controller acquires the still image signal while acquiring the moving image signal from the radiation detector during the cycle of the moving image capturing mode. Consequently, while moving images are being successively acquired, still images of high quality can be acquired between the moving images, in synchronism with capturing of radiographic images by repeatedly capturing a moving image, a still image, and a moving image.

The detector controller may acquire the moving image signal according to a binning process, so that moving images having a high S/N ratio can be acquired.

The radiographic apparatus may further comprise a display device for simultaneously displaying a moving image based on the moving image signal, and a still image based on the still image signal. Therefore, the moving image and the still image can simultaneously be observed on the display device.

According to the present invention, there is also provided a radiographic method to be carried out by a detector controller for switching a radiation detector, which has a matrix of pixels arranged in rows and columns for converting radiation into signal charges, storing the signal charges, and outputting the stored signal charges as a moving image signal or a still image signal, into a moving image capturing mode or a still image capturing mode by controlling storage periods during which the radiation is converted into signal charges and the signal charges are stored, and readout periods during which the stored signal charges are read, the radiographic method comprising the steps of setting a sum of the storage period and the readout period for the still image signal to an integral multiple of a cycle of the moving image capturing mode, in a case where the detector controller acquires the still image signal while acquiring the moving image signal from the radiation detector during the cycle of the moving image capturing mode, and controlling a timing to acquire the still image signal in a cycle, which is an integral multiple of the cycle of the moving image capturing mode.

As described above, the sum of the storage period and the readout period for the still image signal is set to an integral multiple of a cycle of the moving image capturing mode, in a case where the detector controller acquires the still image signal while acquiring the moving image signal from the radiation detector during the cycle of the moving image capturing mode. Further, a timing to acquire the still image signal is controlled in a cycle, which is an integral multiple of the cycle of the moving image capturing mode. Consequently, while moving images are being successively acquired, still images of high quality can be acquired between the moving images in synchronism with capturing of radiographic images by repeatedly capturing a moving image, a still image, and a moving image.

According to the present invention, as described above, while moving images are being successively acquired, still images of high quality can be acquired between the moving images in synchronism with capturing of radiographic images by repeatedly capturing a moving image, a still image, and a moving image.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

A radiographic system incorporating a radiographic apparatus according to an embodiment of the present invention will be described in detail below with reference to the accompanying drawings.

Figure 1:
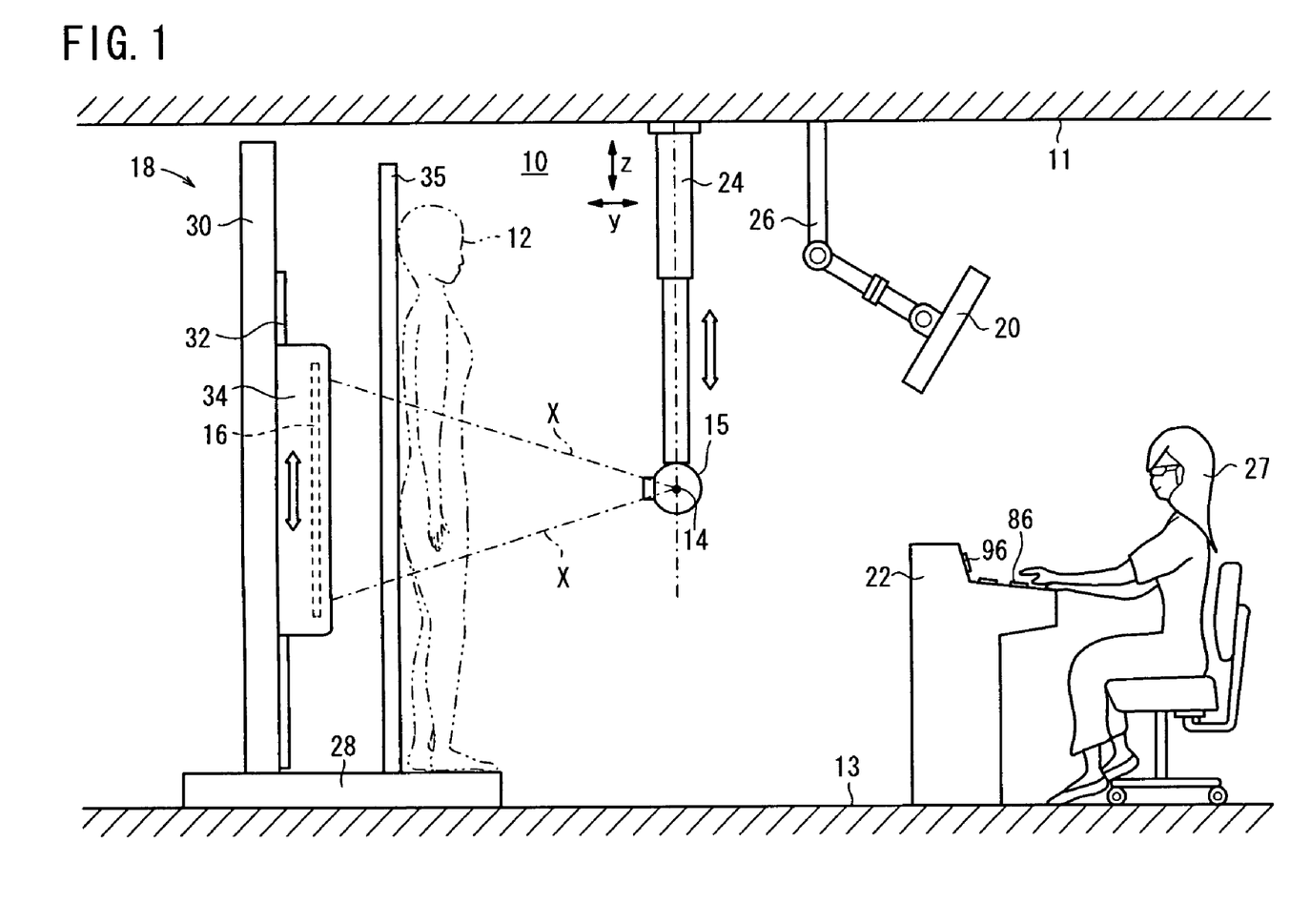
FIG. 1 is a schematic view of an overall arrangement of a radiographic system, which incorporates a radiographic apparatus according to an embodiment of the present invention.
Figure 2:
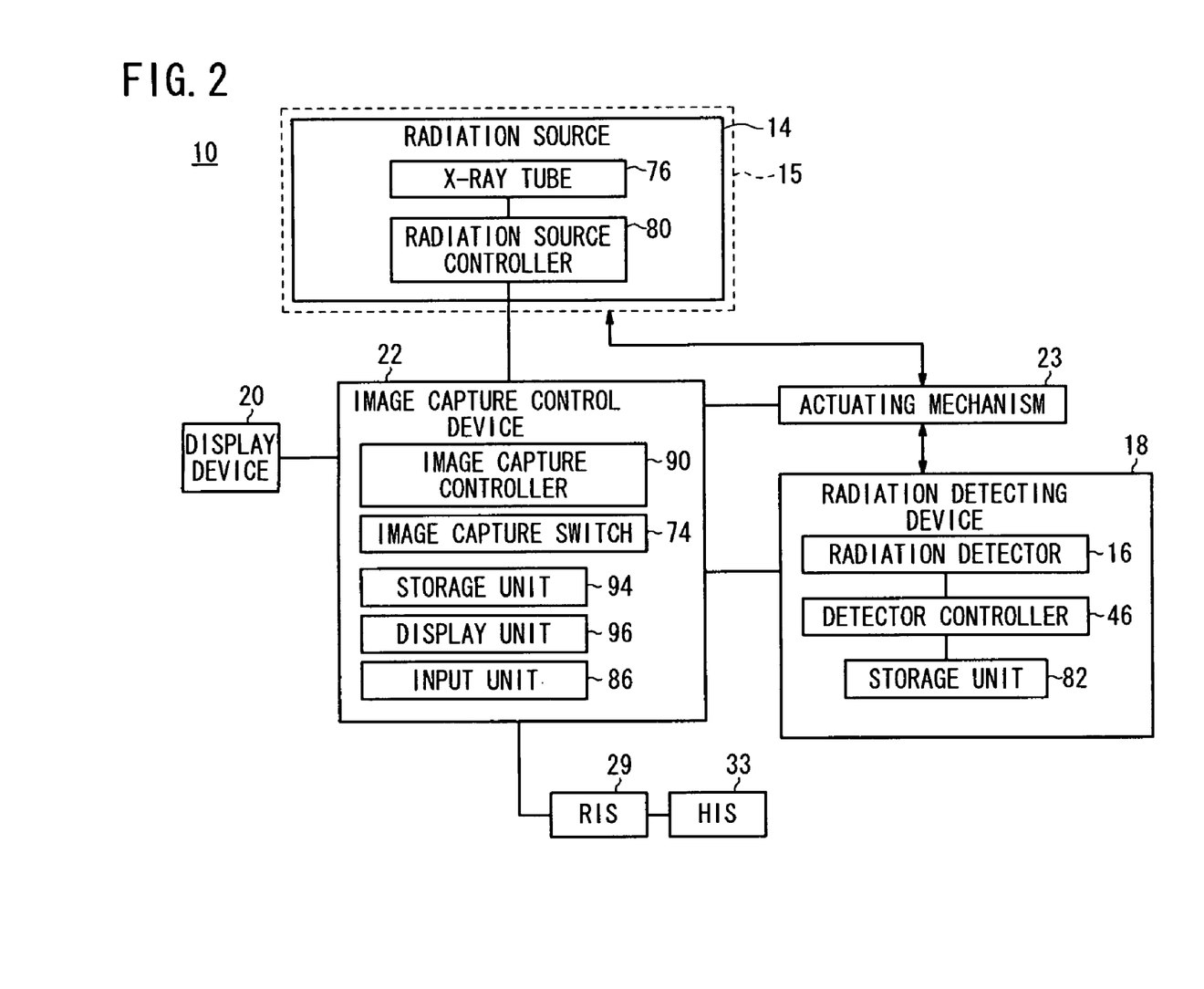
FIG. 2 is a block diagram of the radiographic system.

FIG. 1 shows an overall arrangement of a radiographic system 10, which incorporates therein a radiographic apparatus according to an embodiment of the present invention. FIG. 2 is a block diagram of the radiographic system 10 shown in FIG. 1.

As shown in FIGS. 1 and 2, the radiographic system 10, which typically is installed in a chamber for capturing radiographic images of an examinee using radiation X in a hospital, includes a radiation source 14, which is housed in a tube holder 15, for irradiating the examinee (subject, patient) 12 with radiation X having a dose according to image capturing conditions, a radiation detecting device 18 having a radiation detector 16 {FPD (Flat Panel Detector): flat detector} for detecting radiation X that has passed through the examinee 12, a display device 20 for displaying a radiographic image based on radiation X that is detected by the radiation detecting device 18, an image capture control device (console) 22 for controlling the radiographic system 10 as a whole, and an actuating mechanism 23 (not shown in FIG. 1) for moving the tube holder 15 and the radiation detecting device 18 by means of actuators such as motors or the like under the control of the image capture control device 22. The actuating mechanism 23 moves the tube holder 15 along a vertical direction, i.e., the direction indicated by the arrow Z.

Image capturing conditions are conditions for determining a tube voltage, a tube current, an irradiation time, etc., at which radiation X having an appropriate dose is applied to a region to be imaged of the examinee 12. Such image capturing conditions include, for example, the region to be imaged, and image capturing processes such as a moving image capturing mode, a still image capturing mode, etc.

As shown in FIG. 2, the radiation detecting device 18 comprises the radiation detector 16, a detector controller 46, a storage unit (image memory) 82, and a battery (not shown).

The radiation source 14, the radiation detecting device 18, the display device 20, and the actuating mechanism 23 are connected to the image capture control device 22 by means of wireless or wired communication links, so as to enable signals to be exchanged therebetween.

As shown in FIG. 1, the radiation source 14 is connected to an extensible and contractible arm 24, which extends from the ceiling 11. When radiographic images of the examinee 12 are captured, the extensible and contractible arm 24 can be vertically extended or contracted by the actuating mechanism 23 to a desired position corresponding to a region to be imaged of the examinee 12 when an input unit 86 of the image capture control device 22 is operated by an operator 27. The operator 27 may be a doctor, a radiological technician, or the like. The input unit 86 includes a control lever such as a joystick, switches, a keyboard, a mouse, etc. The input unit 86 is operated by the operator 27 in order to switch between a moving image capturing mode and a still image capturing mode, as well as to change between display patterns on the display device 20.

The display device 20 is connected to a universal arm 26, which extends from the ceiling 11. The display device 20 can be moved and rotated, either manually or by the actuating mechanism 23, to a position where radiographic images displayed on the display device 20 can easily be observed and confirmed by the operator 27.

The radiation detecting device 18 comprises an image capturing table 28 on which the examinee 12 is placed, a support column 30 vertically mounted on the image capturing table 28, a guide rail 32 disposed on and extending along the support column 30, a radiation detecting unit 34 mounted vertically and movably on the guide rail 32, and a screen 35 vertically mounted on the image capturing table 28 and providing a vertical surface against which the examinee 12 can be held. The radiation detecting unit 34 houses the radiation detector 16 therein.

Figure 3:
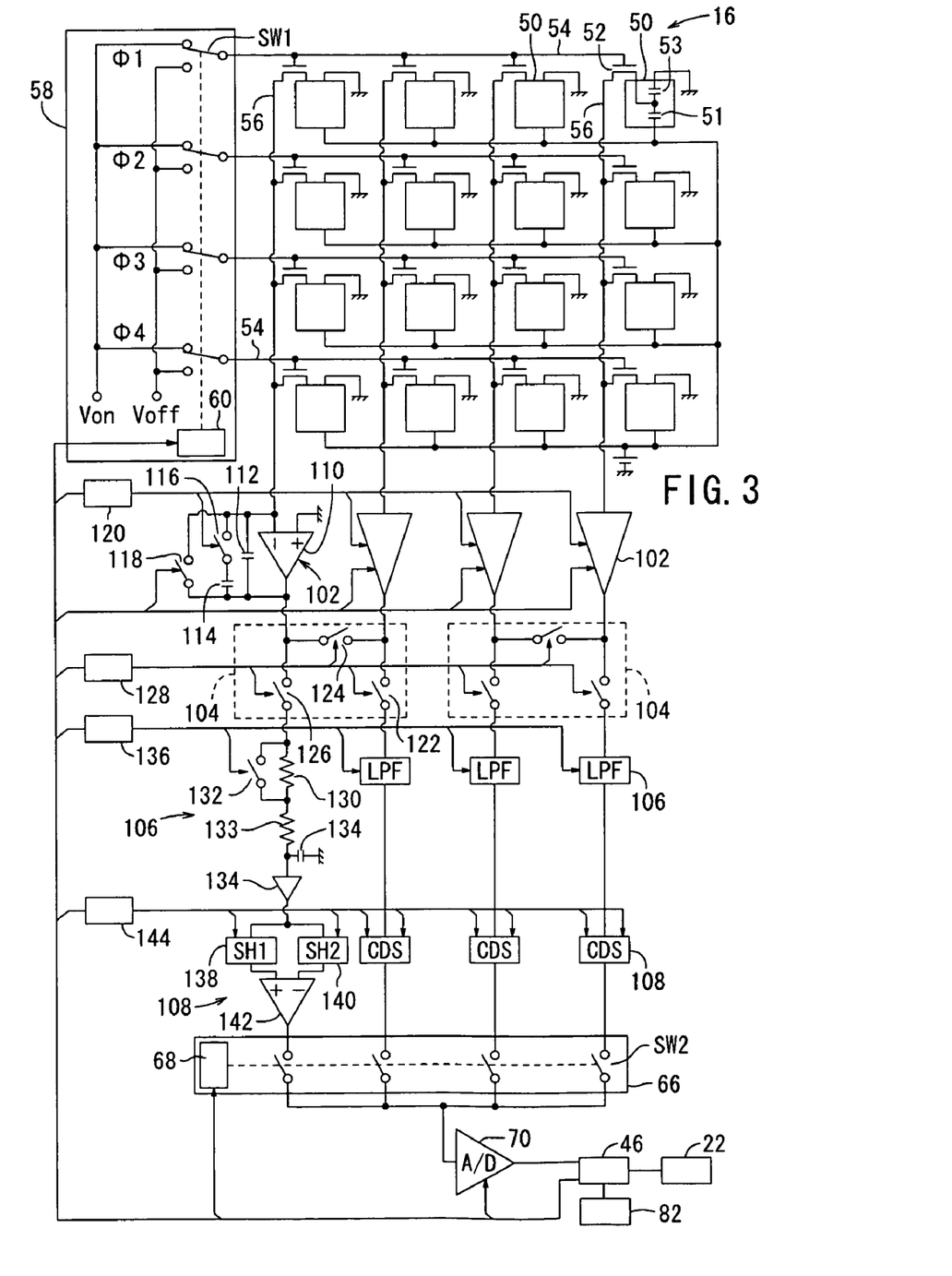
FIG. 3 is a block diagram showing a circuit arrangement of a radiation detecting device.

FIG. 3 shows in block form a circuit arrangement of the radiation detector 16. As shown in FIG. 3, the radiation detector 16 comprises a matrix of thin-film transistors (TFTs) 52 arranged in rows and columns, and a photoelectric conversion layer 51 made up from a material such as amorphous selenium (a-Se) or the like, for detecting radiation X and generating electric charges depending on the detected radiation X. The photoelectric conversion layer 51 is disposed on the array of TFTs 52. After electric charges generated by the photoelectric conversion layer 51 have been stored in storage capacitors (storage components) 53, rows of the TFTs 52 are turned on successively in order to read the stored electric charges as an image signal.

In FIG. 3, details of only one pixel 50, which comprises a photoelectric conversion layer 51 and one storage capacitor 53, and a connection between the pixel 50 and one TFT 52 are illustrated. Details of other pixels 50 are omitted from illustration. To facilitate understanding of operational timings of the radiation detector 16, the radiation detector 16 is shown as comprising 4×4 pixels 50. In actuality, however, the radiation detector 16 comprises one to two million pixels.

The TFTs 52, which are connected respectively to the pixels 50, are connected to gate lines 54 that extend in parallel to the respective rows, and to signal lines 56 that extend in parallel to the respective columns. The gate lines 54 are connected to a line scanning driver 58, and the signal lines 56 are connected to a multiplexer 66 through a reading circuit, which comprises variable-gain preamplifiers (charge amplifiers) 102, binning units 104, LPFs (Low-Pass Filters) 106 with switchable low-pass frequencies, and CDSs (Correlated Double Samplers) 108.

Each of the variable-gain preamplifiers 102 comprises an operational amplifier 110 having a positive input terminal connected to ground, a capacitor 112 connected between the negative input terminal and output terminal of the operational amplifier 110, a switch 116 and a capacitor 114, which are connected in parallel to the capacitor 112 between the negative input terminal and output terminal of the operational amplifier 110, and a resetting switch 118, which is connected in parallel to the switch 116 and the capacitor between the negative input terminal and output terminal of the operational amplifier 110. The switch 116 is controlled so as to be opened and closed by a gain controller 120. The resetting switch 118 is controlled so as to be opened and closed by the detector controller 46.

Each of the binning units 104 comprises a switch 124 connected between adjacent communication lines, and switches 122, 126 connected respectively to the adjacent communication lines. The switches 124, 122, 126 are controlled so as to be opened and closed by a binning controller 128.

Figure 4A:
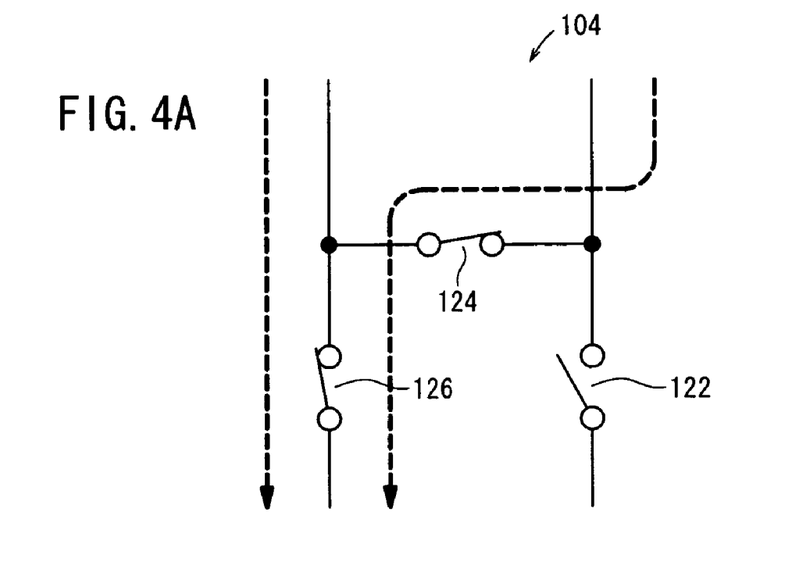
FIG. 4A is a circuit diagram of a binning unit while in the process of carrying out a binning process.
Figure 4B:
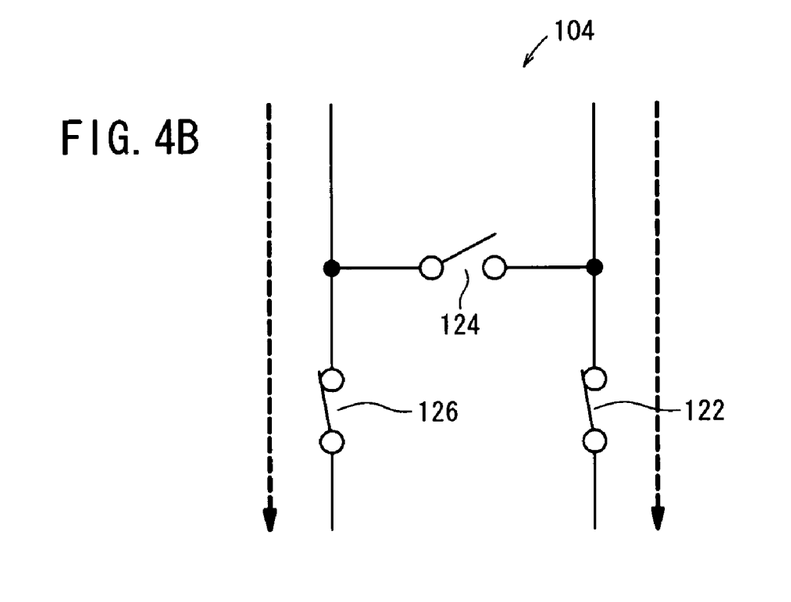
FIG. 4B is a circuit diagram of the binning unit while in the process of carrying out a non-binning process.

For reading an image signal in a moving image capturing mode, the switches 124, 122, 126 are operable to provide a binning connection in each of the binning units 104, as shown in FIG. 4A. With the binning connection, each of the binning units 104 operates in a binning process. For reading an image signal in a still image capturing mode, the switches 124, 122, 126 are operable to provide a normal connection in each of the binning units 104, as shown in FIG. 4B. In a normal connection, each of the binning units 104 operates in a non-binning process.

In FIG. 3, each of the LPFs 106 comprises a resistor 130, another resistor 133 connected in series with the resistor 130, a capacitor 134 connected between an end of the resistor 133 remote from the resistor 130 and ground, and a switch 132 connected across the resistor 130 for shunting the resistor 130. The switch 132 is controlled so as to be opened and closed by a variable LPF controller 136.

Each of the CDSs 108 comprises a first sample and hold circuit 138 for sampling/holding a residual component (noise component) of the signal charges, a second sample and hold circuit 140 for sampling/holding signal charges (noise component+signal component), and a differential amplifier 142 for outputting a voltage signal, which is free of noise components and is representative of signal charges indicative of the signal component only. Sampling timings of the first and second sample and hold circuits 138, 140 are controlled by a CDS controller 144.

The gate lines 54 are supplied with control signals Von (clock pulses $\phi 1$, $\phi 2$, $\phi 3$, $\phi 4$) and Voff for turning on and off the rows of the TFTs 52 from the line scanning driver 58. The line scanning driver 58 includes a plurality of switches SW1 for selecting the gate lines 54, and an address decoder 60 for outputting a selection signal for selecting one of the switches SW1 at a time. The detector controller 46 supplies an address signal to the address decoder 60.

The signal lines 56 are supplied with electric charges, which are stored in the storage capacitors 53 of the respective pixels 50 via the columns of the TFTs 52. The electric charges are converted by the reading circuit, i.e., the variable-gain preamplifiers 102, the binning units 104, the LPFs 106, and the CDSs 108, into voltage signals, which are supplied to the multiplexer 66.

The multiplexer 66 comprises a plurality of switches SW2 for selecting from among the signal lines 56, and an address decoder 68 for outputting a selection signal for selecting one of the switches SW2 at a time. The detector controller 46 supplies an address signal to the address decoder 68.

The multiplexer 66 has output terminals connected to an A/D converter 70, A/D conversion timings of which are controlled by the detector controller 46. The A/D converter 70 converts voltage signals from the CDSs 108 into digital signals, which are representative of radiographic image data produced by the radiation detector 16. The digital signals are stored as radiographic image data in a storage unit 82, which is associated integrally with the radiation detector 16.

The TFTs 52, which function as switching elements, may be combined with another imaging device such as a CMOS (Complementary Metal-Oxide Semiconductor) image sensor or the like. The TFTs 52 may be replaced with a CCD (Charge-Coupled Device) image sensor, which shifts and transfers electric charges together with shift pulses, corresponding to gate signals used for the TFTs.

In FIG. 2, the image capture control device 22 is connected to a radiology information system (RIS) 29 (not shown) that generally manages radiographic image information and other information handled in the radiological department of a hospital. The RIS 29 is connected to a hospital information system (HIS) 33 (not shown) that generally manages medical information in the hospital.

The radiation source 14 includes an X-ray tube 76 for emitting radiation X, and a radiation source controller 80 for controlling the dose (intensity) and irradiation timing of the radiation X. Actually, the radiation source controller 80 is controlled for a given irradiation timing by the detector controller 46 and an image capture controller 90.

When the radiation source controller 80 of the radiation source 14 detects that an image capture switch 74 has been turned on, the radiation source controller 80 energizes the X-ray tube 76 so as to emit radiation X based on image capturing conditions supplied from the image capture control device 22.

The radiation detecting device 18 includes the detector controller 46 and the storage unit 82, in addition to the radiation detector 16. The detector controller 46 acquires radiographic image data produced by the radiation detector 16, and stores the acquired radiographic image data in the storage unit 82.

The image capture control device 22 includes the input unit 86, the image capture switch 74, the image capture controller 90, a storage unit 94, and a display unit 96.

Immediately after an image capturing process has been performed, radiographic image data stored in the storage unit 82 of the radiation detecting device 18 are transferred to the storage unit 94 of the image capture control device 22. The radiographic image data then are processed by the image capture controller 90, in accordance with a predetermined image processing process. The processed radiographic image data are supplied to the display device 20, which based on the radiographic image data, displays a radiographic image of a body region of the examinee 12 either as a moving image or a still image.

The radiographic system 10 according to the present embodiment basically is constructed as described above. Next, operations of the radiographic system 10 will be described.

The image capture control device 22 monitors whether or not the image capture control device 22 is supplied with an image capturing order via the RIS 29. When an image capturing order (image capturing conditions) including examinee information is supplied to the image capture control device 22, the display unit 96 displays the image capturing order.

The image capture controller 90 selects an image capture menu (e.g., image capturing conditions that indicate capturing of an image of all of the lower limbs) corresponding to the image capturing order.

The image capture controller 90 then controls the actuating mechanism 23 in order to move the radiation source 14 to a position corresponding to the image capture menu.

The operator 27 places the examinee 12 on the image capturing table 28, positions the examinee 12 against the screen 35, and secures the examinee 12 to the screen 35 with a fastening belt.

Then, according to the image capturing conditions, the operator 27 operates the input unit 86 to select one of the moving image capturing mode and the still image capturing mode, and turns on the image capture switch 74. Thereafter, the X-ray tube 76 is energized according to the image capturing conditions to apply radiation X to the examinee 12.

Radiation X that has passed through the examinee 12 is detected by the pixels 50 of the radiation detector 16. When application of radiation X is finished, electric charges are read from the pixels 50 and converted by the A/D converter 70 into digital signals representative of digital radiographic image data, which are stored in the storage unit 82.

Operation timings of the moving image capturing mode and the still image capturing mode will be described below with reference to the timing charts shown in FIGS. 5 through 7.

[General Description of Moving Image Capturing Mode and Still Image Capturing Mode]

Figure 5:
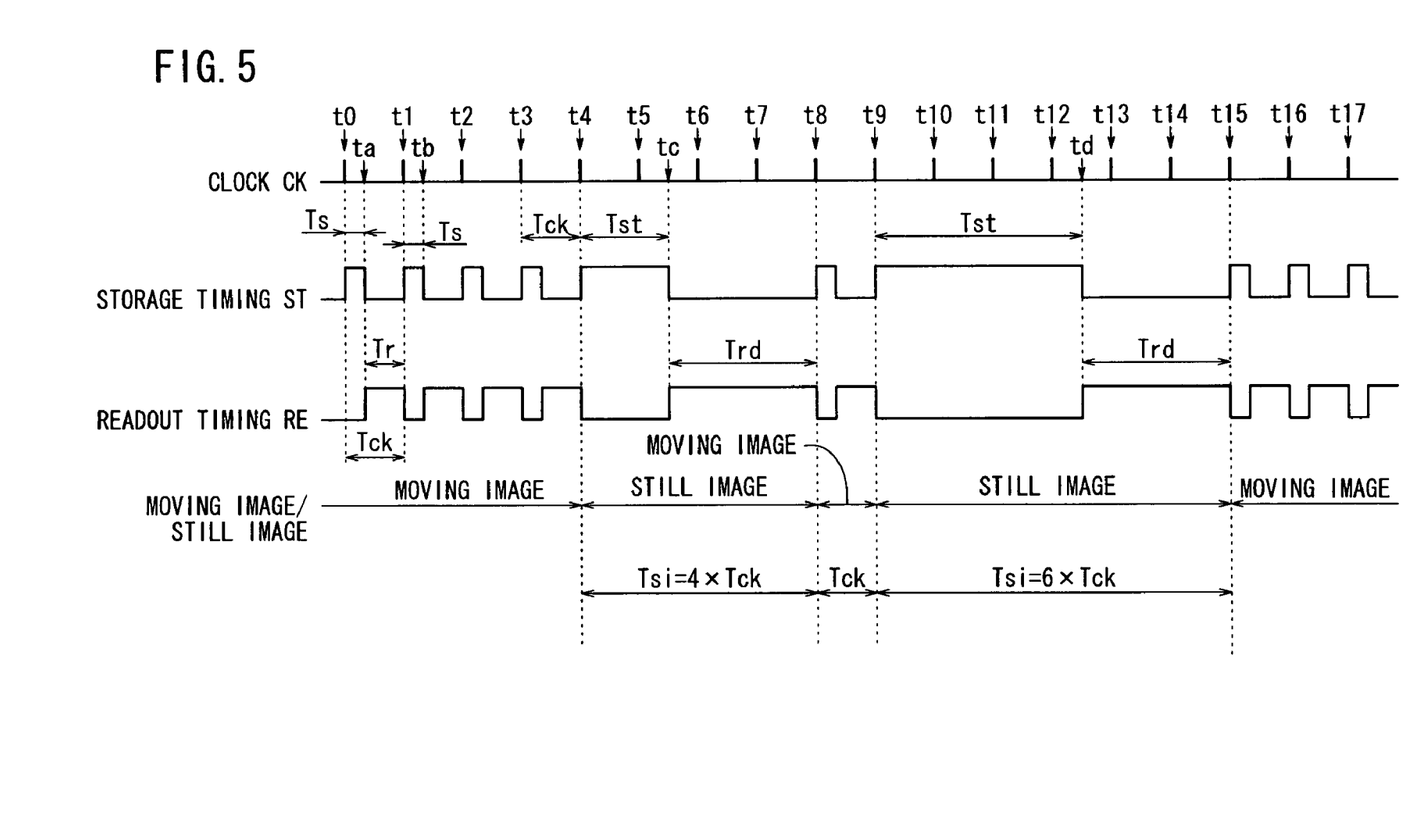
FIG. 5 is a timing chart showing a relationship between timings used to capture moving and still images according to the present embodiment.

FIG. 5 shows the relationship between timings for capturing moving images and timings for capturing still images according to the present embodiment.

FIG. 5 illustrates a clock signal CK that determines image capturing timings. The clock signal CK has cycles that function as moving image capturing mode cycles (also referred to as clock cycles) Tck=1/30 [sec]=33.3 [ms]. Therefore, the radiographic system 10 is capable of capturing 30 frames per second in the moving image capturing mode. Alternatively, the radiographic system 10 may captures 10 or 100 frames per second in the moving image capturing mode. The clock cycles Tck correspond to cycles at a vertical synchronizing frequency of a video signal.

In FIG. 5, time t0 to time t4 serves as a period for capturing a moving image, time t4 to time t8 serves as a period for capturing a still image, time t8 to time t9 serves as a period for capturing a moving image, time t9 to time t15 serves as a period for capturing a still image, and time t15 to t17 serves as a period for capturing a moving image.

When the input unit 86 initially enters an instruction for the moving image capturing mode, four frames of a moving image are captured from time t0 to time t4 in the moving image capturing mode. If the input unit 86 enters an instruction for the still image capturing mode during a period up to time t4, and if the still image capturing period Tsi indicated by the instruction is Tsi=4×Tck, then a still image is captured from time t4 to time t8. At time t8, the still image capturing mode automatically changes back to the moving image capturing mode.

If the input unit 86 enters an instruction for the still image capturing mode during a period up to time t9, and if the still image capturing period Tsi indicated by the instruction is Tsi=6×Tck, then a still image is captured during the still image capturing period Tsi from time t8 to time t15. At time t15, the still image capturing mode automatically changes back to the moving image capturing mode.

The still image capturing period Tsi is represented by the sum of the storage period Tst and the readout period Trd (Tsi=Tst+Trd). Since the still image capturing period Tsi is set to an integral multiple of the moving image capturing mode cycle Tck (storage period Ts+readout period Tr), radiographic images are captured in synchronism by repeatedly capturing a moving image (from time t0 to time t4, or from time t8 to time t9), a still image (from time t4 to time t8, or from time t9 to time t15), and a moving image (from time t8 to time t9, or from time t15 to time t17). While moving images are acquired successively, high-quality still images that are captured during the storage period Tst, which is longer than the storage time Ts for the moving images, can be acquired between the moving images.

Radiation X is applied to the examinee 12 for a given period, which is slightly shorter than the storage period Ts and the storage period Tst according to the storage timing ST. Radiation X is not applied to the examinee 12 for the subsequent readout period Tr and the readout period Trd. Radiation X is applied at an irradiation timing, which is controlled in synchronism with the storage timing ST.

The dose of radiation X, which is applied during the still image capturing mode, is at least twice the dose of radiation X applied during the moving image capturing mode. Generally, the dose of radiation X that is applied in the still image capturing mode has a large level, i.e., at least ten times the dose of radiation X applied during the moving image capturing mode.

The storage period Ts for storing moving images is set to about 1 to 5 [ms], whereas the storage period Tst for storing still images is set to about 20 to 500 [ms].

Readout periods Tr, Trd are determined depending on the panel size and the number of pixels. If the panel size is a half size (17 inches×14 inches), then the readout period Tr for reading moving images is set to about 28 [ms], and the readout time Trd for reading still images is set to about 180 [ms].

[Moving Image Capturing Mode]

When the moving image capturing mode is selected on the input unit 86 of the image capture control device 22 prior to time t0, the detector controller 46 and the binning controller 128 control the binning units 104 so as to operate in the binning process shown in FIG. 4A. At the same time, since the dose of applied radiation X is relatively small in the moving image capturing mode, the gain controller 120 opens the switches 116 in order to increase the gain of the variable-gain preamplifiers 102. The resetting switches 118 are placed in an open state due to the low level of the resetting signal RT.

In the moving image capturing mode, in order to increase response rather than reducing noise, the variable LPF controller 136 closes the switches 132 in order to shift a low-pass frequency fc of the LPFs 106 to a higher frequency.

During the storage period Ts from time t0 to time ta, according to the storage timing ST as shown in FIG. 5, radiation X that has passed through the examinee 12 is applied to the photoelectric conversion layer 51 of the pixels 50, which converts the radiation X into electric charges. The electric charges are stored in the storage capacitors 53.

Figure 6:
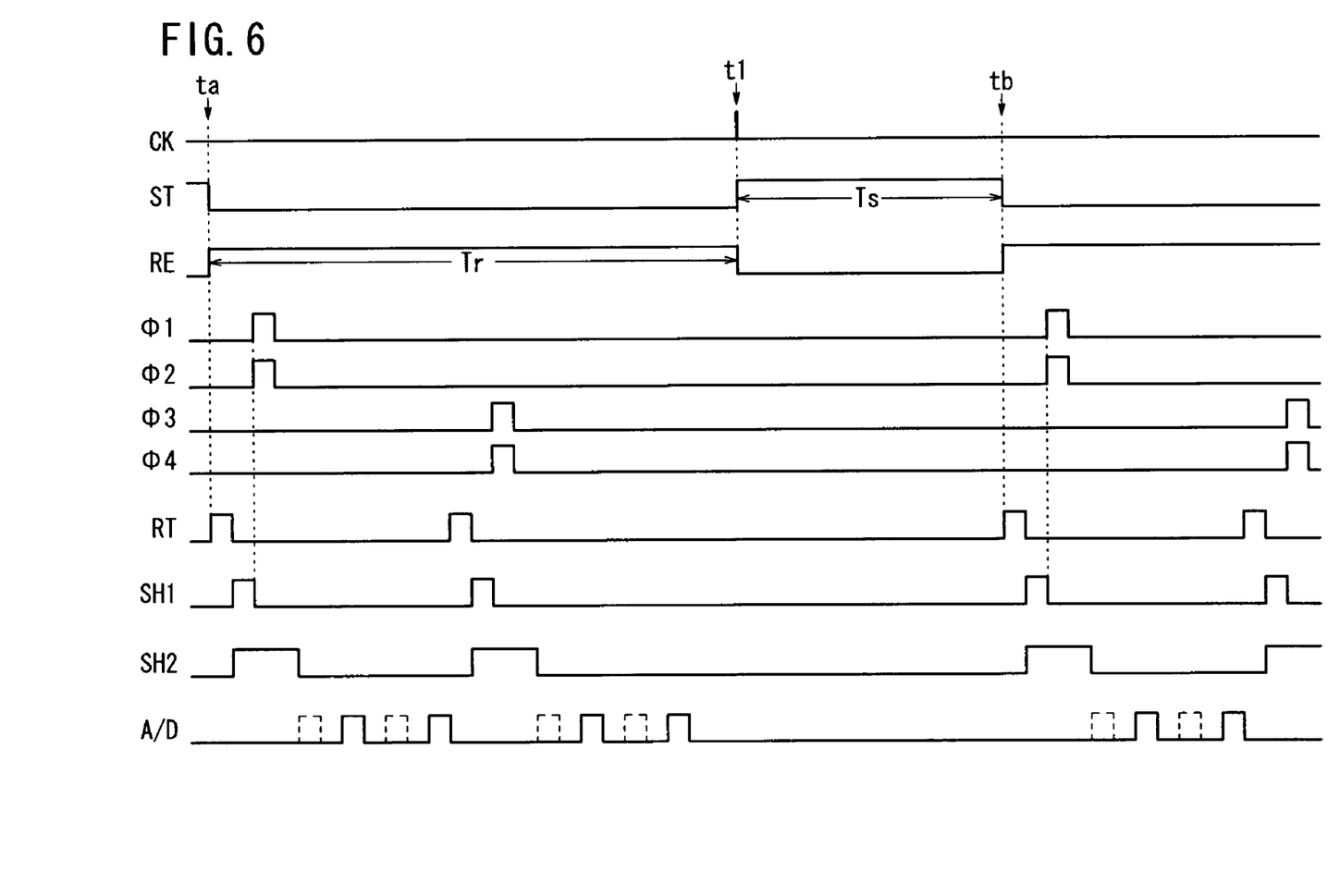
FIG. 6 is a timing chart of a moving image capturing mode.

FIG. 6 illustrates, at an enlarged scale, timings of the moving image capturing mode from time ta to time tb shown in FIG. 5. As shown in FIG. 6, a readout timing RE (readout period Tr) starts at time ta. First, the resetting switches 118 of the variable-gain preamplifiers 102 are closed by the resetting signal RT, thereby discharging the electric charges stored in the capacitors 112, 114.

Then, the CDS controller 144 energizes the first sample and hold circuits (SH1) 138 for a prescribed period, thereby holding a noise level.

Then, at the same time, the readout clock pulses φ1, φ2 go high, simultaneously turning on the TFTs 52 of the pixels 50, which belong to the first and second rows from above as shown in FIG. 3. The signal charges flow from the storage capacitors 53 of such pixels 50, and are amplified by the variable-gain preamplifiers 102.

At this time, the amplified signal charges from the four right pixels 50 of the first and second rows from above are combined by the right binning unit 104 shown in FIG. 3. Also, the amplified signal charges from the four left pixels 50 of the first and second rows from above are combined by the left binning unit 104 shown in FIG. 3.

The signal charges, which are combined by the right binning unit 104, flow through the second LPF 106 from the right into the energized second sample and hold circuit (SH2) 140 of the second CDS 108 from the right. The second sample and hold circuit (SH2) 140 holds a level, which is representative of the sum of the noise level and the signal charges.

At the same time, the signal charges combined by the left binning unit 104 flow through the leftmost LPF 106 into the energized second sample and hold circuit (SH2) 140 of the leftmost CDS 108. The second sample and hold circuit (SH2) 140 holds a level, which is representative of the sum of the noise level and the signal charges.

At this time, the differential amplifier 142 of the second CDS 108 from the right produces, at the output terminal thereof, a differential voltage (i.e., a signal voltage) between the output signal from the first sample and hold circuit 138 and the output signal from the second sample and hold circuit 140. Similarly, the differential amplifier 142 of the leftmost CDS 108 produces, at the output terminal thereof, a differential voltage (i.e., a signal voltage) between the output signal from the first sample and hold circuit 138 and the output signal from the second sample and hold circuit 140.

The signal voltage from the second CDS 108 from the right, and the signal voltage from the leftmost CDS 108 are converted respectively and successively by the A/D converter 70 into digital image signals representative of combined signal charges from the four right pixels 50 of the first and second rows from above, and digital image signals representative of combined signal charges from the four left pixels 50 of the first and second rows from above. The detector controller 46 operates to store such digital image signals in the storage unit 82.

Likewise, the readout clock pulses φ3, φ4 go high simultaneously prior to time t1. A digital image signal, which represents the combined signal charges from the four right pixels 50 of the third and fourth rows from above, and a digital image signal, which represents the combined signal charges from the four left pixels 50 of the third and fourth rows from above, are produced. The detector controller 46 operates to store such digital image signals in the storage unit 82.

Therefore, digital image signals from the four pixel sets, each comprising 2×2 pixels, which make up all of the sixteen pixels 50 shown in FIG. 3, are obtained as one frame of moving image data. In this manner, four frames of moving image data are obtained until time t4 (see FIG. 5).

Digital image signals stored as moving image data in the storage unit 82 are then transferred to the storage unit 94 of the image capture control device 22. The image capture controller 90 expands, by way of interpolation, the digital image signals into one frame (one screen) of moving image data covering 4×4 pixels, which make up all the pixels 50 of the radiation detector 16 shown in FIG. 3. The image capture controller 90 then sends the aforementioned one frame of moving image data as a video signal to the display device 20.

Figure 8:
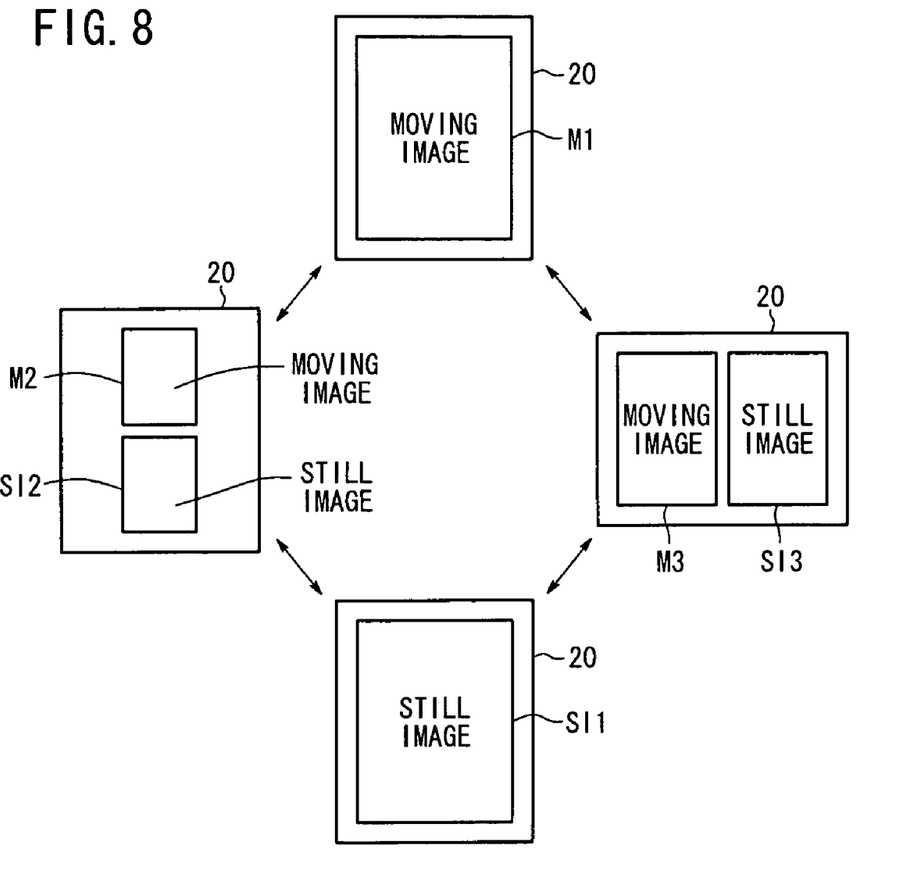
FIG. 8 is a diagram showing various display patterns on a display device.

As shown in FIG. 8, at this time, the operator 27 can observe a moving image M1, which is displayed on the display device 20 based on the video signal.

[Still Image Capturing Mode]

When the still image capturing mode is selected on the input unit 86 of the image capture control device 22, during a period until time t4 shown in FIG. 5, the detector controller 46 and the binning controller 128 control the binning units 104 to operate in a non-binning process, as shown in FIG. 4B. At the same time, since the dose of the applied radiation X is relatively large in the still image capturing mode, the gain controller 120 closes the switches 116 in order to reduce the gain of the variable-gain preamplifiers 102, and to prevent the variable-gain preamplifiers 102 from becoming saturated. The resetting switches 118 are placed in an open state due to the low level of the resetting signal RT.

In order to reduce noise and to achieve higher image quality in the still image capturing mode, the variable LPF controller 136 opens the switches 132 in order to shift the low-pass frequency fc of the LPFs 106 to a lower frequency.

During a storage period Tst from time t4 to time tc, according to the storage timing ST shown in FIG. 5, radiation X that has passed through the examinee 12 is applied to the photoelectric conversion layer 51 of the pixels 50, which converts the radiation X into electric charges. The electric charges are stored in the storage capacitors 53.

Figure 7:
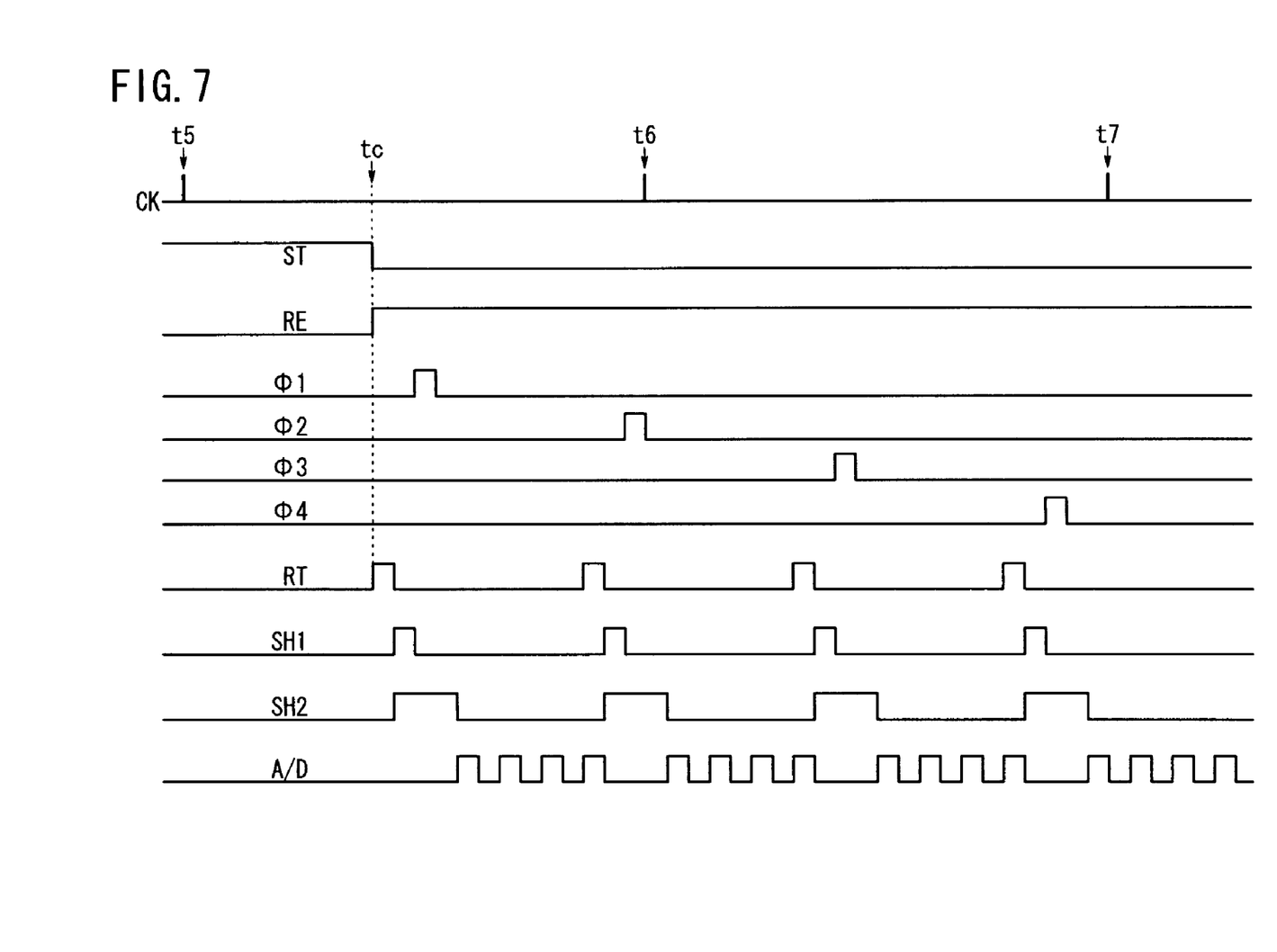
FIG. 7 is a timing chart of a still image capturing mode.

FIG. 7 illustrates, at an enlarged scale, timings of the still image capturing mode, which take place from time t5 to time t7 in FIG. 5. As shown in FIG. 7, a readout timing RE (readout period Trd) starts at time tc. First, the resetting switches 118 of the variable-gain preamplifiers 102 are closed by the resetting signal RT, thereby discharging the electric charges stored in the capacitors 112, 114.

Then, the CDS controller 144 energizes the first sample and hold circuits (SH1) 138 for a prescribed period, thereby holding a noise level.

Then, the readout clock pulses $\phi 1$, $\phi 2$, $\phi 3$, $\phi 4$ successively go high, and the radiation detecting device 18 operates in a manner similar to the moving image capturing mode, in order to store digital image signals from 4×4 pixels, which make up sixteen pixels 50 of the radiation detector 16, in the storage unit 82 under the control of the detector controller 46.

Therefore, the digital image signals from the 4×4 pixels, which make up sixteen pixels 50 in total, are obtained as one screen of still image data.

The digital image signals, which are stored as still image data in the storage unit 82, then are transferred to the storage unit 94 of the image capture control device 22. The image capture controller 90 sends the digital image signals as a video signal to the display device 20.

As shown in FIG. 8, the operator 27 can now observe a still image SI1, which is displayed on the display device 20 based on the video signal.

As shown in FIG. 8, the moving image M1 and the still image SI1 can be scaled down to a moving image M3 and a still image SI3, respectively, so that the moving image M1 and the still image SI1 can simultaneously be displayed on the display device 20 as a horizontal array of images. The moving image M1 and the still image SI1 can also be scaled down to a moving image M2 and a still image SI2, respectively, so that the moving image M1 and the still image SI1 can simultaneously be displayed on the display device 20 as a vertical array of images.

General Description of the Embodiment

According to the present embodiment, as described above, the radiographic system 10 includes the radiation detector 16 having pixels 50, which are arranged in rows and columns for converting radiation X into signal charges, storing the signal charges, and outputting the stored signal charges as a moving image signal or a still image signal. The radiographic system 10 also includes the detector controller 46 for switching the radiation detector 16 into a moving image capturing mode or a still image capturing mode by controlling storage periods Ts, Tst during which the radiation X is converted into signal charges and the signal charges are stored, and readout periods Tr, Trd during which the stored signal charges are read. The detector controller 46 controls a timing to acquire the still image signal such that a sum (Tst+Trd) of storage period Tst and readout period Trd for the still image signal is an integral multiple (Ts+Tr=Tck×n, where n is an integer of 2 or greater) of a cycle Tck of the moving image capturing mode, when the detector controller 46 acquires the still image signal while acquiring the moving image signal from the radiation detector 16 during the cycle Tck (Ts+Tr) of the moving image capturing mode.

While moving images are successively acquired, high-quality still images can be acquired between the moving images in synchronism with capturing of radiographic images by repeatedly capturing a moving image, a still image, and a moving image.

When a moving image is to be captured of a concerned body region of the examinee, i.e., a body region of interest, using a contrast agent, the entire image capturing process may not be completed when the moving image is captured and thereafter a still image is captured. In some cases, while the doctor is in the process of diagnosing the moving image, still images of the body region of the examinee, which the doctor has noticed from the moving image, may need to be repeatedly captured. The radiographic apparatus according to the present embodiment is suitable for use in such a situation.

Since the detector controller 46 acquires the moving image signal according to a binning process, the acquired moving image signal has a high S/N ratio.

The display device 20 can simultaneously display a moving image based on a moving image signal, and a still image based on a still image signal. For example, the display device 20 can simultaneously display the moving image M2 and the still image SI2, or the moving image M3 and the still image SI3. Therefore, when a still image of a body region of interest of the examinee 12 is being captured, and while the doctor diagnoses a moving image of the body region that is captured using a contrast agent, both the moving image and the still image of the body region of interest can simultaneously be observed on the display device 20.

Although a certain preferred embodiment of the present invention has been shown and described in detail, it should be understood that various changes and modifications may be made to the embodiment without departing from the scope of the invention as set forth in the appended claims. For example, instead of the above-mentioned radiation detector 16 of direct conversion type using the photoelectric conversion layer 51 made up from a material such as a-Se or the like, an indirect-type radiation converter may be used. Such indirect type radiation converter has a scintillator which converts radioactive rays into fluorescent light using a phosphor such as CsI:Tl (thallium-doped cesium iodide), CsI:Na (sodium-activated cesium iodide), GOS ($Gd_2O_2S$:Tb) and the like, and photo-electrically converts the fluorescent light by a photo-diode.

What is claimed is:

1. A radiographic apparatus comprising:
    a radiation detector having a matrix of pixels arranged in rows and columns for converting radiation into signal charges, storing the signal charges, and outputting the stored signal charges as a moving image signal or a still image signal; and
    a detector controller for switching the radiation detector into a moving image capturing mode or a still image capturing mode, by controlling at least storage periods during which the radiation is converted into the signal charges and the signal charges are stored, and readout periods during which the stored signal charges are read,
    wherein the detector controller controls a timing to acquire the still image signal, such that a sum of the storage period and the readout period for the still image signal is an integral multiple of a cycle of the moving image capturing mode, in a case where the detector controller acquires the still image signal while acquiring the moving image signal from the radiation detector during the cycle of the moving image capturing mode.

2. The radiographic apparatus according to claim 1, wherein the detector controller acquires the moving image signal according to a binning process.

3. The radiographic apparatus according to claim 1, further comprising:
 a display device for simultaneously displaying a moving image based on the moving image signal and a still image based on the still image signal.

4. A radiographic method to be carried out by a detector controller for switching a radiation detector, which has a matrix of pixels arranged in rows and columns for converting radiation into signal charges, storing the signal charges, and outputting the stored signal charges as a moving image signal or a still image signal, into a moving image capturing mode or a still image capturing mode, by controlling at least storage periods during which the radiation is converted into the signal charges and the signal charges are stored, and readout periods during which the stored signal charges are read, the radiographic method comprising the steps of:
 setting a sum of the storage period and the readout period for the still image signal to an integral multiple of a cycle of the moving image capturing mode, in a case where the detector controller acquires the still image signal while acquiring the moving image signal from the radiation detector during the cycle of the moving image capturing mode; and
 controlling a timing to acquire the still image signal in a cycle, which is the integral multiple of the cycle of the moving image capturing mode.

* * * * *